United States Patent
Murphy et al.

(10) Patent No.: US 9,968,270 B1
(45) Date of Patent: May 15, 2018

(54) DETERMINATION OF PULSE RATE RECOVERY

(71) Applicant: Verily Life Sciences LLC, Mountain View, CA (US)

(72) Inventors: Mark Murphy, Palo Alto, CA (US); Philip John Stephens, Thousand Oaks, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 101 days.

(21) Appl. No.: 14/989,564

(22) Filed: Jan. 6, 2016

(51) Int. Cl.
  *A61B 5/024* (2006.01)
  *A61B 5/0245* (2006.01)
  *G06F 19/00* (2018.01)
  *A61B 5/00* (2006.01)

(52) U.S. Cl.
  CPC ............ *A61B 5/0245* (2013.01); *A61B 5/024* (2013.01); *A61B 5/02427* (2013.01); *A61B 5/7235* (2013.01); *G06F 19/3406* (2013.01)

(58) Field of Classification Search
  CPC ... A61B 5/024; A61B 5/0245; A61B 5/02416; A61B 5/7235
  See application file for complete search history.

(56) References Cited

U.S. PATENT DOCUMENTS

| | | | |
|---|---|---|---|
| 5,976,083 A * | 11/1999 | Richardson | A61B 5/0245 482/8 |
| 2015/0119728 A1 | 4/2015 | Blackadar et al. | |
| 2015/0126824 A1 | 5/2015 | LeBoeuf et al. | |
| 2015/0141766 A1 | 5/2015 | Fine | |
| 2015/0164322 A1 | 6/2015 | Derchak | |
| 2015/0208986 A1 | 7/2015 | Gottesman | |

* cited by examiner

*Primary Examiner* — Tammie K Heller
(74) *Attorney, Agent, or Firm* — McDonnell Boehnen Hulbert & Berghoff LLP

(57) ABSTRACT

Example embodiments assess cardiovascular health by receiving, from at least one monitoring device, pulse rate data from a subject. The pulse rate data includes pulse rate measurements and corresponding measurement timestamps. The embodiments select, with at least one processor, a plurality of recovery periods in the pulse rate data. Each recovery period corresponds to a respective decrease in pulse rate from a respective upper pulse rate to a respective lower pulse rate. The respective upper pulse rate is less than a peak pulse rate of the subject or the respective lower pulse rate is greater than a resting pulse rate of the subject. The embodiments determine, with the at least one processor, an exponential decay from the plurality of selected recovery periods. The exponential decay characterizes a pulse rate recovery for the subject. The embodiments provide, via a user interface, the pulse rate recovery based on the exponential decay.

20 Claims, 9 Drawing Sheets

DETERMINATION OF PULSE RATE RECOVERY

BACKGROUND

Unless otherwise indicated herein, the materials described in this section are not prior art to the claims in this application and are not admitted to be prior art by inclusion in this section.

To evaluate the physical fitness of a subject, a medical practitioner may observe the subject's physiological response when the subject engages in some physical activity. For instance, an evaluation may involve observing how the subject's pulse rate responds while the subject experiences a heightened level of exertion. Such observations by the medical practitioner typically occur in a controlled clinical setting.

SUMMARY

Example embodiments employ a system of sensors that can collect information relating to the subject's cardiovascular health while the subject is away from the medical practitioner. Without directly observing the subject's activity, the medical practitioner can evaluate the subject's cardiovascular fitness from the information collected by the sensors.

Specifically, the example embodiments can collect pulse rate data from the subject while the subject engages in physical activity outside a controlled clinical setting. In contrast to controlled clinical procedures, the example embodiments can accurately characterize pulse rate recovery from pulse rate data collected during non-prescribed physical activities and uncontrolled recovery periods. For instance, the example embodiments can determine the exponential decay associated with the subject's pulse rate recovery, even if the pulse rate does not reach the subject's peak pulse rate during the physical activities or does not decrease to the subject's resting pulse rate during the recovery periods. The rate of exponential decay is an indicator of the subject's ability to recover from physical activity and can be used to evaluate cardiovascular health.

In an example embodiment, a system for assessing cardiovascular health, includes at least one monitoring device configured to collect pulse rate data from a subject. The pulse rate data includes pulse rate measurements and corresponding measurement timestamps. The at least one monitoring device includes a first communication interface. The system includes a controller. The controller includes a second communication interface configured to be communicatively coupled to the first communication interface of the at least one monitoring device and receive the pulse rate data from the at least one monitoring device. The controller includes at least one data storage device configured to store the pulse rate data on the at least one data storage device. The controller includes at least one processor. The controller selects a plurality of recovery periods in the pulse rate data. Each recovery period corresponds to a respective decrease in pulse rate from a respective upper pulse rate to a respective lower pulse rate. The respective upper pulse rate is less than a peak pulse rate of the subject or the respective lower pulse rate is greater than a resting pulse rate of the subject. The controller determines an exponential decay from the plurality of selected recovery periods. The exponential decay characterizes a pulse rate recovery for the subject. The controller provides, via a user interface, the pulse rate recovery for the subject based on the exponential decay.

In another example embodiment, a method for assessing cardiovascular health includes receiving, from at least one monitoring device, pulse rate data from a subject. The pulse rate data includes pulse rate measurements and corresponding measurement timestamps. The method includes storing the pulse rate data on at least one data storage device. The method includes selecting, with at least one processor, a plurality of recovery periods in the pulse rate data. Each recovery period corresponds to a respective decrease in pulse rate from a respective upper pulse rate to a respective lower pulse rate. The respective upper pulse rate is less than a peak pulse rate of the subject or the respective lower pulse rate is greater than a resting pulse rate of the subject. The method includes determining, with the at least one processor, an exponential decay from the plurality of selected recovery periods. The exponential decay characterizes a pulse rate recovery for the subject. The method includes providing, via a user interface, the pulse rate recovery for the subject based on the exponential decay.

In yet another embodiment, a method for assessing cardiovascular health includes receiving, from at least one monitoring device, more than one set of pulse rate data from a subject. Each set of pulse rate data is collected during a respective data collection period and includes pulse rate measurements and corresponding measurement timestamps. The method includes selecting, with at least one processor, a set of recovery periods from each set of pulse rate data. Each recovery period corresponds to a respective decrease in pulse rate from a respective upper pulse rate to a respective lower pulse rate. The respective upper pulse rate is less than a peak pulse rate of the subject or the respective lower pulse rate is greater than a resting pulse rate of the subject. The method includes determining, with the at least one processor, an exponential decay from each set of selected recovery periods. Each exponential decay characterizes a pulse rate recovery for the subject for the respective data collection period. The method includes providing, via a user interface, a comparison of the pulse rate recoveries from the data collection periods based on the exponential decays.

These as well as other aspects, advantages, and alternatives, will become apparent to those of ordinary skill in the art by reading the following detailed description, with reference where appropriate to the accompanying drawings.

Figure 1:
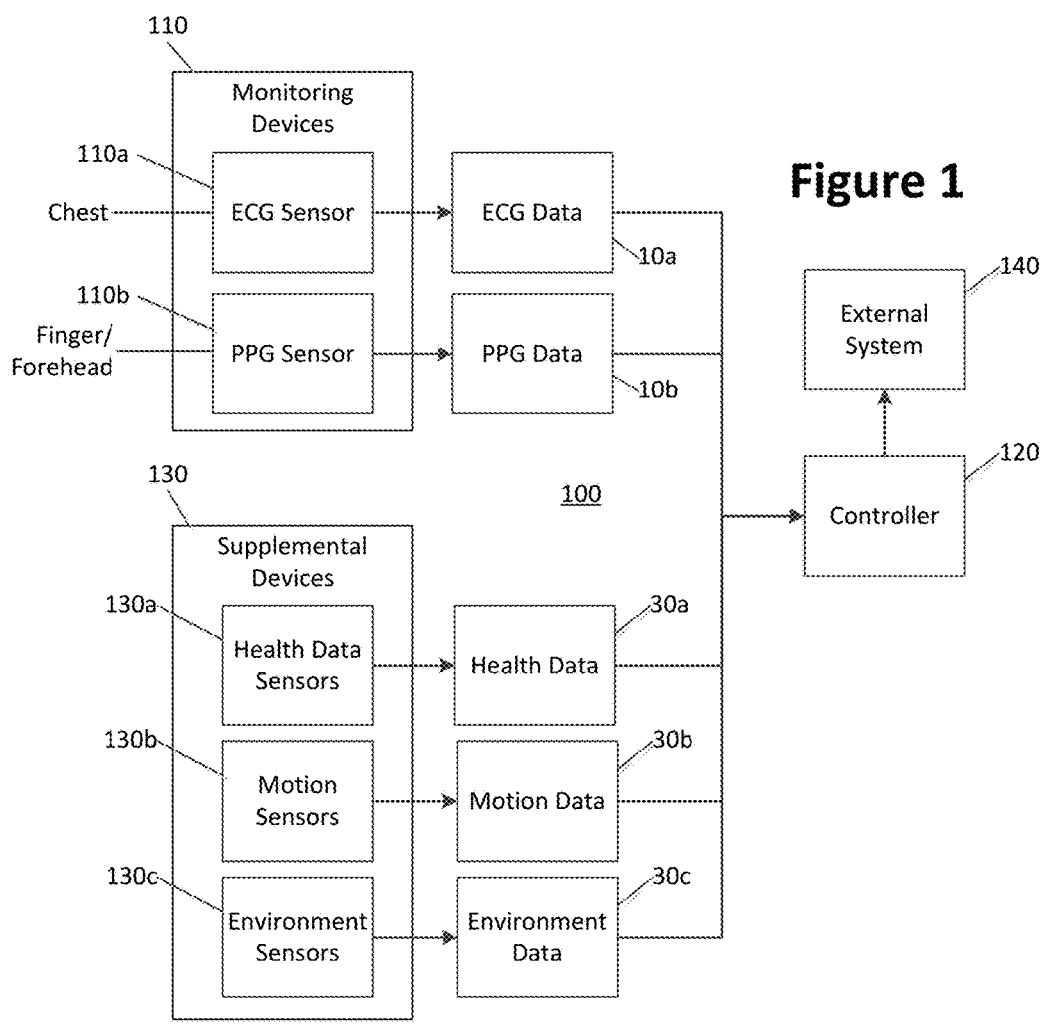
FIG. 1 illustrates an example monitoring system that includes cardiovascular monitoring devices that may collect data relating to the subject's pulse rate.

While the invention is susceptible to various modifications and alternative forms, specific embodiments have been shown by way of example in the Figures and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims. It should be understood that other embodiments may include more or less of each element shown in a given Figure. Further, some of the illustrated elements may be combined or omitted. Yet further, an example embodiment may include elements that are not illustrated in the Figures.

DETAILED DESCRIPTION

The following detailed description describes various features and functions of the disclosed systems and methods with reference to the accompanying figures. In the Figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Overview

When a subject engages in physical activity, the subject's pulse rate increases to satisfy the body's increased demand for oxygen and need to expel carbon dioxide. The ability of the cardiovascular system to recover from the increased pulse rate, also known as pulse rate recovery, is an indicator of cardiovascular health. Cardiovascular health can be evaluated according to the amount of time needed for the pulse rate to decrease to a resting pulse rate.

To evaluate the cardiovascular health of a subject, a medical practitioner may observe the subject's pulse rate recovery after the subject engages in some physical activity. For instance, in a controlled clinical procedure, the subject runs on a treadmill at the subject's peak level of exertion to reach a peak pulse rate. The peak pulse rate at a given time may occur at or near the subject's highest possible pulse rate in response to the highest possible level of exertion. Following a specified duration of peak pulse rate, the subject steps off the treadmill and assumes a supine or other resting position. While the subject remains in this position, the medical practitioner collects pulse rate data for several minutes as it decreases following the cessation of exertion. Collecting the pulse rate data according to a controlled clinical procedure helps to ensure that sufficient data is collected to characterize the pulse rate recovery accurately.

Although the clinical procedure may provide a useful snapshot of the subject's cardiovascular health, the medical practitioner may want to track changes in the subject's cardiovascular health. Tracking such changes, however, may involve repeated visits to the medical practitioner to collect several snapshots of the subject's cardiovascular health over time. Health care costs, however, can increase significantly with each visit. In addition, repeated visits to the medical practitioner may be burdensome and inconvenient. Furthermore, between visits by the subject, the medical practitioner is not able to monitor the subject and may not be able to collect data that indicate important changes in the subject's cardiovascular health.

To minimize the number of visits to the medical practitioner and to allow the medical practitioner to obtain more frequent information, example embodiments employ a system of sensors that can collect information relating to the subject's cardiovascular health while the subject is away from the medical practitioner. Without directly observing the subject's activity, the medical practitioner can evaluate the subject's cardiovascular fitness from the information collected by the sensors.

Specifically, the example embodiments can collect and process pulse rate data from the subject while the subject engages in physical activity outside a controlled clinical setting. In contrast to controlled clinical procedures, the example embodiments can accurately characterize pulse rate recovery from pulse rate data collected during non-prescribed physical activities and uncontrolled recovery periods. For instance, the example embodiments can determine the exponential decay associated with the subject's pulse rate recovery, even if the pulse rate does not reach the subject's peak pulse rate during the physical activities or does not decrease to the subject's resting pulse rate during the recovery periods. The rate of exponential decay is an indicator of the subject's ability to recover from physical activity and can be used to evaluate cardiovascular health. The resting pulse rate at a given time may occur at or near the subject's lowest possible heart rate when the subject is at complete rest after several minutes (e.g., 20 to 30 minutes) of inactivity. The average resting pulse rate for a person in good health, for instance, may be between 60 and 75 beats per minute (BPM), while athletes in excellent condition may have resting pulse rates as low as 40 to 50 BPM.

II. Example Embodiments for Collecting Data

FIG. 1 illustrates an example monitoring system 100 that includes cardiovascular monitoring devices 110 that may collect data relating to the subject's pulse rate. For instance, as shown in FIG. 1, the cardiovascular monitoring devices 110 may include an electrocardiography (ECG) sensor 110a and/or a photoplethysmography (PPG) sensor 110b. The cardiovascular monitoring devices 110 allow measurements to be taken continuously over a period of time and can be used during physical activity.

The ECG sensor 110a may collect data 10a relating to electrical activity in the subject's heart. The ECG sensor 110a may include electrodes that are placed, for instance, on the subject's chest. The electrodes detect electrical signals on the skin that arise as the heart experiences a pattern of depolarization/repolarization during each cardiac cycle. Depolarization corresponds to contraction of a heart muscle and occurs when an electrical impulse causes ions to move across heart cell membranes. Repolarization corresponds to relaxation of heart muscle and occurs when the ions return to a resting state. The heart generally experiences a repeating cycle of atrial depolarization, atrial repolarization, ventricular depolarization, and ventricular repolarization. The ECG data 10a provides information on the pattern of depolarization/repolarization over repeating cardiac cycles. A tracing of the ECG data 10a, for instance, may show the pattern as a series of waves including a P wave corresponding to the atrial depolarization, QRS wave corresponding to the ventricular depolarization, and a T wave corresponding to the ventricular repolarization. Instantaneous pulse rate (e.g., heartbeats/minute) can be determined from the R wave-to-R wave (RR) interval.

Additionally or alternatively, the example monitoring system 100 may employ the PPG sensor 110b to collect data 10b relating to changes in blood volume in a body part as the subject's heart pumps blood. The photoplethysmography (PPG) sensor 110b may employ a pulse oximeter, which includes a light source, such as a light-emitting diode (LED), and a photodetector, such as a photodiode. The light source illuminates tissue and the photodetector measures the light intensity after the light passes through the tissue. In some embodiments, for instance, the PPG sensor 110b may be coupled to the subject's finger. In such cases, the light source is disposed on one side of the finger and the photodetector is disposed on an opposing side of the finger. The photodetector detects light from the light source after it passes from one side of the finger to the other.

In other embodiments, for instance, the PPG sensor 110b may be coupled to the subject's forehead. Thus, the light source and the photodetector are disposed on the same side of the body part. The photodetector detects light from the light source after it enters the forehead and is reflected back to the surface by tissue in the forehead.

With each cardiac cycle, the heart pumps blood to the finger or forehead to increase blood volume. This change in blood volume increases the optical density of the tissue and, to a lesser degree, lengthens the path for the light travelling from the light source to the photodetector. Thus, with each pulse of blood, more light is absorbed by the tissue and the photodetector measures less light intensity. The measurements of light intensity change in response to the pumping of the heart over repeating cardiac cycles. Thus, the PPG data 10b provides information relating to the blood volume in the body part based on these measurements of light intensity. Aspects of the PPG data 10b are directly attributable to variation in blood volume caused by the pressure pulse of the repeating cardiac cycles. As such, the pulse rate can be determined from the PPG data 10b.

Although the cardiovascular monitoring devices 110 shown in FIG. 1 may include the ECG sensor 110a and/or the PPG sensor 110b, the cardiovascular monitoring devices 110 may additionally or alternatively include other types of sensors that employ any number of different technologies to measure indicators of cardiovascular function, including pulse rate, blood flow, blood pressure, or the like. Alternatively or additionally, other cardiovascular monitoring devices 110 may also employ Doppler ultrasound, laser Doppler flowmetry (LDF), laser speckle imaging (LSI), magnetic resonance imaging (MRI), ultrasonic echocardiography, tonometry, sphygmomanometry, and impedance cardiography.

Figure 2:
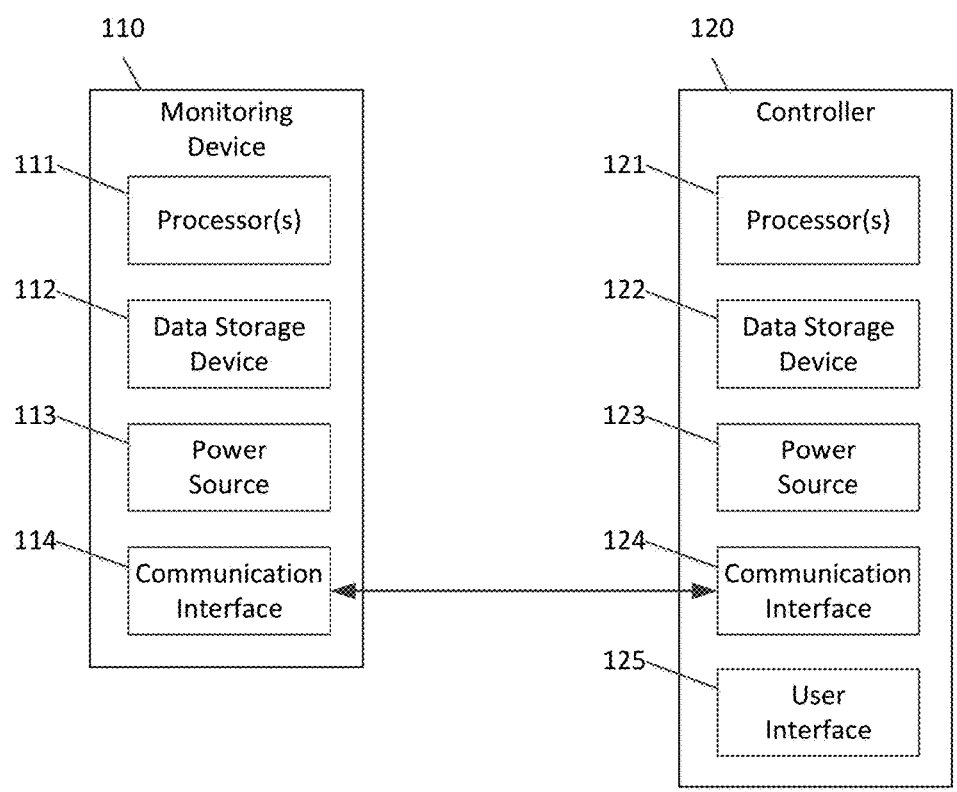
FIG. 2 illustrates an example monitoring device and controller for collecting and processing data relating to a subject's cardiovascular function.

As shown in FIG. 2, each cardiovascular monitoring device 110 may include at least one processor 111, at least one data storage device 112, a power source 113, and a communication interface 114. The at least one processor 111 manages the general operation of the cardiovascular monitoring device(s) 110 to collect data relating to pulse rates and optionally other indicators of cardiovascular function. The at least one data storage device 113 may include non-volatile memory, such as flash memory, to store the data collected by the cardiovascular monitoring device 110. The power source 113, such as a disposable or rechargeable battery, powers the general operation of the motion sensor device 110.

As FIG. 1 illustrates, the example monitoring system 100 also includes a controller 120. The sensors 110a, b transmit the respective data 10a, b to the controller 120 for processing. As shown in FIG. 2, the controller 120 includes at least one processor 121, at least one data storage device 122, a power source 123, at least one communication interface 124, and a user interface 125. The at least one data storage device 122 may store program instructions that can be executed by the at least one processor 121 to manage and process the collection of data by the cardiovascular monitoring devices 110.

The at least one communication interface 124 allows the controller 120 to be communicatively coupled to each cardiovascular monitoring device 110 via the respective communication interface 114. For instance, the controller 120 can communicate with one or more of the cardiovascular monitoring devices 110, for example using a BLUETOOTH® or BLUETOOTH® LOW ENERGY (BLE) (2.4 to 2.485 GHz UHF) wireless connection. Additionally or alternatively, the controller 120 can communicate with one or more of the cardiovascular monitoring devices 110 using a WIFI™ (IEEE 802.11) wireless connection. Additionally or alternatively, the controller 120 can communicate with one or more of the cardiovascular monitoring devices 110 via wired connection.

The controller 120 can signal the cardiovascular monitoring devices 110 via the communication interfaces 114, 124 to collect data. The controller 120 can specify particular modes for data collection. The modes can determine when the data collection should take place (e.g., period of time) and/or how frequently the data should be collected. The modes can determine which of the available cardiovascular monitoring devices 110 should be activated to collect data and what data should be collected.

In response to the controller 120, the cardiovascular monitoring devices 110 collect data relating to pulse rate and optionally other cardiovascular function. Each cardiovascular monitoring device 110 may store the collected data on the at least one data storage device 112 at least temporarily, and the data may be subsequently transmitted to the controller 120 via the communication interfaces 114, 124. The controller 120 may then store the collected data from the cardiovascular monitoring devices 110 on the at least one data storage device 122. The controller 120 may also process the collected data for visual or other presentation on the user interface 125.

To allow the controller 120 to temporally associate the data from the several cardiovascular monitoring devices 110, the collected data may be time-aligned with high precision. For example, the collected data may be time-aligned at ±1 millisecond precision to allow for accurate temporal association. Accordingly, the example monitoring system 100 may employ a network time protocol (NTP) to synchronize the cardiovascular monitoring devices 110. In some cases, the controller 120 is employed to synchronize the cardiovascular monitoring devices 110 with an NTP server. Alternatively, each cardiovascular monitoring device 110 may communicate separately with a common NTP server via the respective communication interface 114.

Additionally or alternatively, the collected data may be time-aligned with an event that is detected by each cardiovascular monitoring device 110. In one example, the controller 120 may emit a signal, e.g., over a wireless communication channel, that the cardiovascular monitoring devices 110 can detect. Thus, the data collected from each cardiovascular monitoring device 110 includes this emitted signal, which can be used to time-align the data from all the cardiovascular monitoring devices 110.

Motion of the body parts during data collection can introduce motion-related artifacts into the collected data. In other words, the cardiovascular monitoring devices 110 may detect signals that result from the motion of body parts. Motion-related artifacts may obscure, distort, or misrepresent the actual cardiovascular data. In addition to motion-related artifacts, the data collected by the monitoring devices 110 may include other types of artifacts. Unless the artifacts can be identified and filtered from the collected data, the collected data may not provide accurate information for the assessment of cardiovascular function.

The example monitoring system 100 can process the collected data to allow cardiovascular function to be accurately evaluated, even if the collected data may include artifacts. In particular, the example monitoring system 100 may collect data simultaneously from multiple monitoring devices 110. The data from these monitoring devices 110 are based on measurements of indicators resulting from the same cardiac activity. The data from the monitoring devices 110 include components that reflect common aspects of the same cardiac activity. As such, the data include components that are correlated. By statistically comparing the data collected from the multiple cardiovascular monitoring devices during the same time period, the example system can identify the correlated components which are attributable to cardiovascular function.

The data from the monitoring devices 110 may also include components that reflect the measurement of artifacts. In contrast to the correlated cardiovascular components, the artifact components may generally be the result of different respective phenomena. For instance, motion-related artifacts may be caused by different motions by different respective body parts. Additionally, artifacts may also result from the operation of a particular type of sensor and the specific type of technology used by that sensor. Thus, the artifact components are generally uncorrelated. Because the artifact components are generally uncorrelated, the process of extracting the correlated cardiovascular components also results in the rejection of the uncorrelated artifact components.

The controller 120 may be a device that is structurally separate from the monitoring devices 110. For instance, the controller 120 may be conveniently worn by the subject as a wrist-worn device. As such, the subject can conveniently control the monitoring devices 110 in a manner similar to the operation of a multi-function digital sports/fitness watch. Alternatively, the control mechanism 120 may be structurally combined with one of the monitoring devices 110.

The example embodiments allow frequent monitoring of the subject and can collect data continuously over extended periods of time when the subject is in a non-clinical setting. To enhance the convenience of collecting such data in a non-clinical setting, the monitoring devices 110 may have non-invasive and non-intrusive configurations. In particular, the monitoring devices 110 may be sufficiently small, discreet, and low-power to be compatible with wearable form factors that allow the subject to conduct different activities during data collection. In general, the example monitoring system 100 is configured so that the monitoring devices 110 can be coupled securely to, and removed from, respective body parts in a convenient and easy manner.

To supplement the cardiovascular data collected by the cardiovascular monitoring devices 110, the example monitoring system 100 may also include supplemental monitoring devices 130 that collect and transmit other types of data to the controller 120. The data from these supplemental monitoring devices 130 may help provide greater context for assessing the collected cardiovascular data. For instance, example monitoring system 100 may include other types of health data sensors 130 to collect health data 30a. The health data sensors 130a, for example, may include body temperature sensors, electroencephalography (EEG) sensors or galvanic skin response (GSR)/skin conductance/electrodermal activity (EDA) sensors, etc.

Additionally or alternatively, the example monitoring system 100 may include one or more motion sensors 130b, which include inertial measurement units (IMUs), accelerometers, or the like. For instance, by collecting data 30b on the movement of the subject and various body parts, for instance, a medical practitioner can determine the subject's activity during collection of the cardiovascular data in a non-clinical setting.

Additionally or alternatively, the example monitoring system 100 may include environmental sensors 130c that provide useful environmental data 30c that may relate to the subject's location, surroundings, and/or the subject's interaction with surrounding objects. For instance, the environmental sensors 130c may include a thermometer to record air temperature during data collection. The environmental sensors 130c may also include a global positioning system (GPS) to capture changes of location as the subject engages in the activity. For instance, by considering GPS data with the motion data, the medical practitioner can determine that the subject was running in the neighborhood and can assess how the subject's pace may indicate the state of the subject's cardiovascular health.

In general, the monitoring system 100 may employ a variety of approaches to classify the types of activity being conducted by the subject. In addition to the use of sensors, the subject may actively input into the monitoring system 100 (e.g., via the user interface 125) information that identifies the subject's activities during respective time periods.

As shown in FIG. 1, the controller 120 may also be configured to transmit the data from the monitoring devices 110, 130 to an external system 140, such as a computer or cloud data storage, where for example a medical practitioner can access the data for analysis. The controller 120 may transmit the data to the external system 140 over a wide-area network (WAN), such as the Internet. The controller 120 may also transmit the data over a short distance to the external system over a wired or wireless connection. For example, the controller 120 may connect with the external system 140 using BLUETOOTH® or BLUETOOTH® LOW ENERGY (BLE) technology via the communication interface 124. In alternative embodiments, the data can be transmitted directly from the monitoring devices 110, 130 via the respective communication interfaces to the external system 140 over similar wired or wireless connections.

III. Example Clinical Procedure for Assessing Pulse Rate Recovery

When the subject engages in physical activity, the subject's pulse rate may increase to satisfy the body's increased demand for oxygen and need to expel carbon dioxide. The ability of the cardiovascular system to recover from the increased pulse rate, also known as pulse rate recovery, is an indicator of cardiovascular health. Cardiovascular health can be evaluated according to the amount of time needed for the pulse rate to decrease to the resting pulse rate.

In a controlled clinical procedure, a medical practitioner may prescribe a specific physical activity for the subject. For example, the prescribed physical activity may involve running on a treadmill. The subject engages in the prescribed physical activity at a peak level of exertion so that the subject reaches a peak pulse rate, e.g., at or near the subject's highest possible pulse rate. The medical practitioner can monitor the subject to ensure that the subject substantially maintains the peak pulse rate during the prescribed physical activity. Following a predetermined amount of time at this peak pulse rate, the subject ends the physical activity and assumes a supine or other resting position. While the subject remains in this position, the medical practitioner collects pulse rate data during a recovery period (e.g., several minutes) following the end of the prescribed physical activity.

Figure 3:
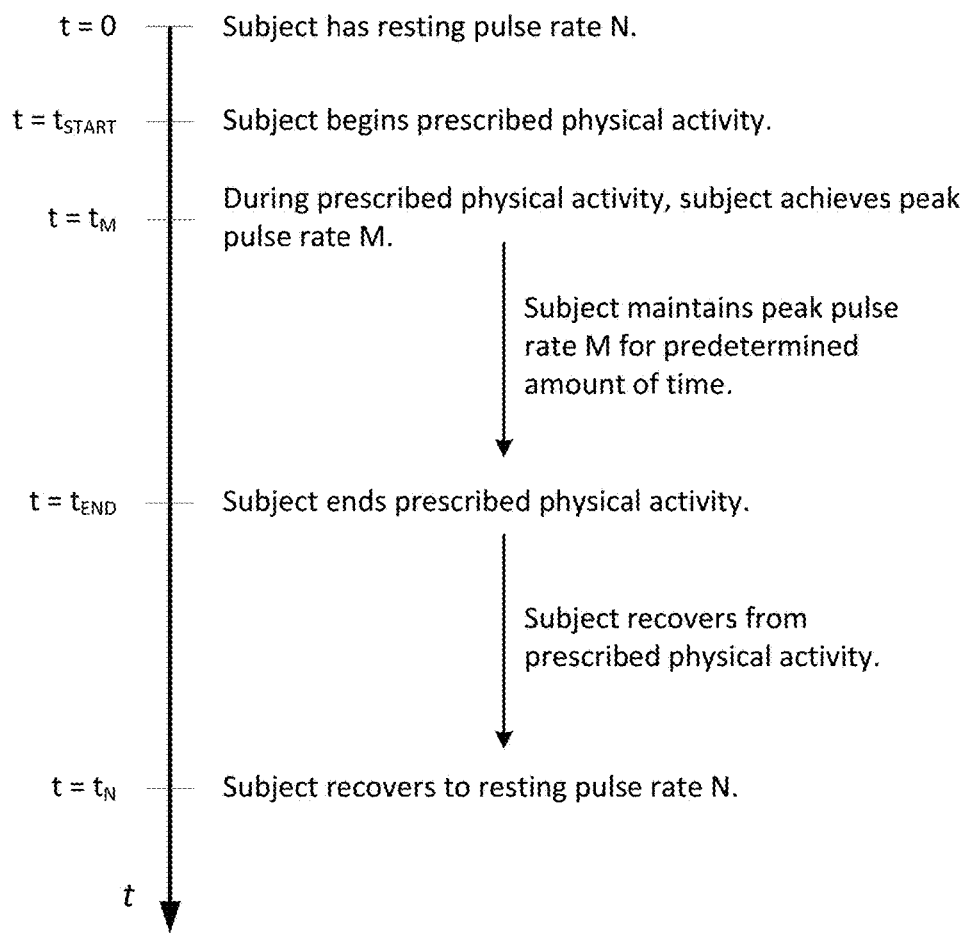
FIG. 3 illustrates a timeline for an example controlled clinical procedure for determining pulse rate recovery.

FIG. 3 illustrates an example controlled clinical procedure. At a time t=0, the subject's pulse rate r is a resting pulse rate N. At a time t t=$t_{START}$, the subject starts the prescribed physical activity and the pulse rate r begins to increase. At a time t=$t_M$, the pulse rate r reaches the subject's peak pulse rate M. The subject maintains the peak pulse rate M for the predetermined amount of time until time t=$t_{END}$. At time t=$t_{END}$, the subject ends the prescribed physical activity. The pulse rate r decreases over the recovery period from the time $t_{END}$ until it reaches the resting pulse rate N at time t=$t_N$.

Between the end of the prescribed physical activity at time t=$t_{END}$ and the end of the recovery period at time t=$t_N$, the pulse rate r generally experiences an exponential decay from the peak pulse rate M to the resting pulse rate N. Thus, the pulse rate recovery is characterized by this exponential decay. In particular, the pulse rate data can be fit to the following pulse rate recovery model:

$$r(t)=N+(M-N)e^{-(t/\tau)} \quad (1)$$

where τ is the exponential time constant (inverse of decay constant λ). Cardiovascular health can be evaluated according to the amount of time needed for the pulse rate to return to the resting pulse rate N. In particular, a faster exponential decay generally indicates better cardiovascular health.

In general, collecting the pulse rate data according to a controlled clinical procedure helps to ensure that sufficient data is collected to characterize the pulse rate recovery. For instance, the medical practitioner can closely supervise the prescribed physical activity to help ensure that the subject experiences maximum exertion and achieves the peak pulse rate M. In addition, after the end of the prescribed physical activity, the medical practitioner can keep the subject in the resting position for a sufficient amount time to allow the pulse rate to decrease until it is substantially equal to the resting pulse rate N.

Although the controlled clinical procedure may provide a useful snapshot of the subject's cardiovascular health, the medical practitioner may want to track changes in the subject's cardiovascular health. Tracking such changes, however, may involve repeated visits to the medical practitioner to collect several snapshots of the subject's cardiovascular health over time. Health care costs, however, can increase significantly with each visit. In addition, repeated visits to the medical practitioner may be burdensome and inconvenient, especially if poor health makes it difficult for the subject to travel. Furthermore, between visits by the subject, the medical practitioner is not able to monitor the subject and may not be able to collect data that indicate important changes in the subject's fitness.

IV. Example Non-Clinical Procedure for Assessing Pulse Rate Recovery

To minimize the number of visits to a medical practitioner and to allow the medical practitioner to obtain more frequent information on the subject's physical fitness, example embodiments may employ the example monitoring system 100 to collect pulse rate data from a subject while the subject is away from the medical practitioner. Even though the subject is in a non-clinical environment and does not engage in prescribed physical activity under the supervision of a medical practitioner, the example embodiments can collect sufficient pulse rate data over a period of time and process the pulse rate data to determine accurately the ability of the subject's cardiovascular activity to recover from physical exertion.

The subject may engage in different types of non-prescribed physical activities in a non-clinical environment over a data collection period T. The data collection period T may have any duration, e.g., several minutes, hours, days, etc. The physical activities, however, do not have to occur continuously over the data collection period T. Additionally, the data collection period T may include periods of sleep or other activities that do not increase the pulse rate significantly. For instance, a subject may engage in separate exercise sessions in a week. Setting the data collection period T to one week, the example embodiments can collect and process pulse rate data from the subject during these separate exercise sessions. Furthermore, the data collection period T may include different types of physical activities. For instance, the separate exercise sessions may involve any of running, cycling, lifting weights, etc., respectively.

Figure 4A:
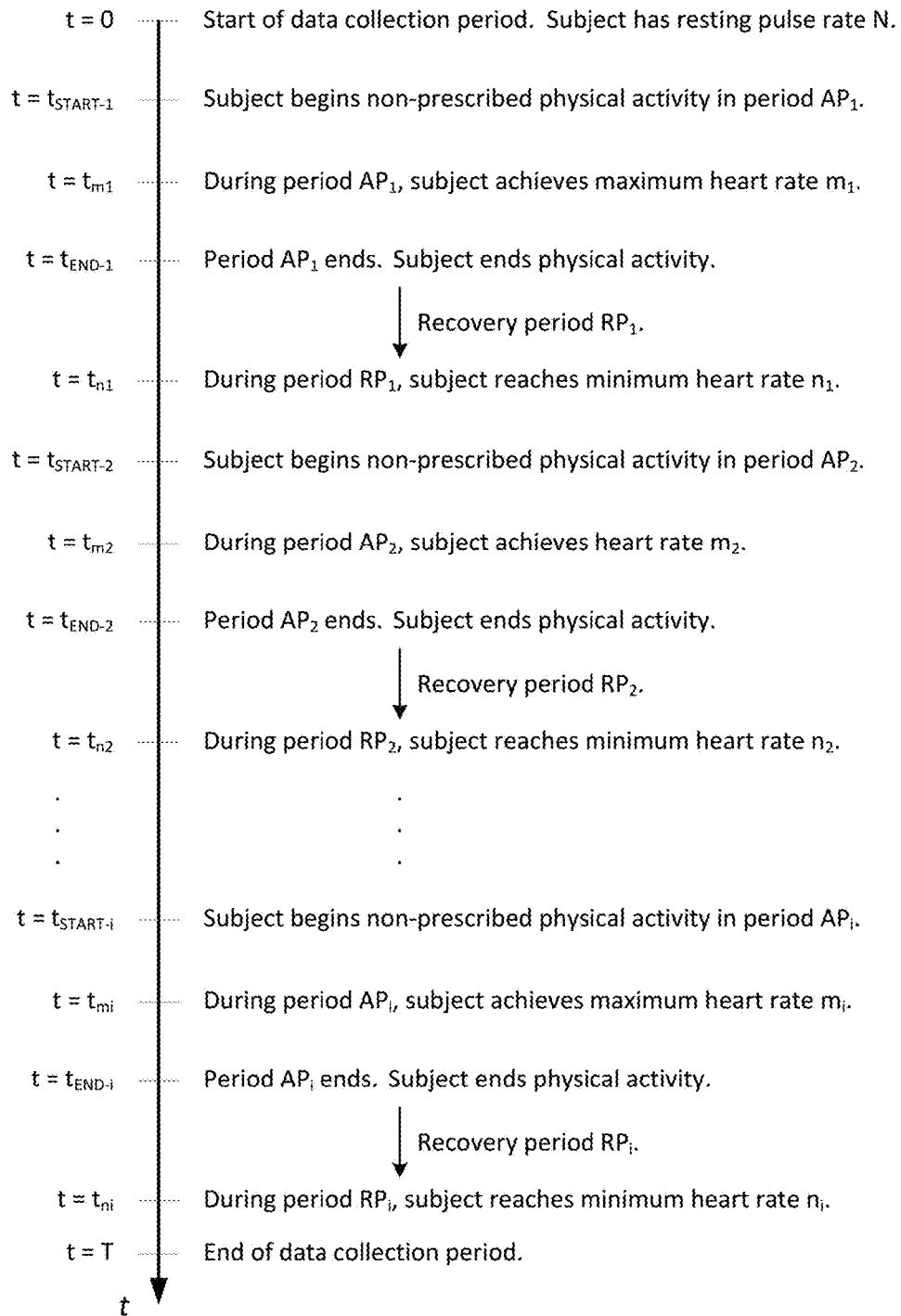
FIG. 4A illustrates a timeline for an example data collection period for determining pulse rate recovery.
Figure 4B:
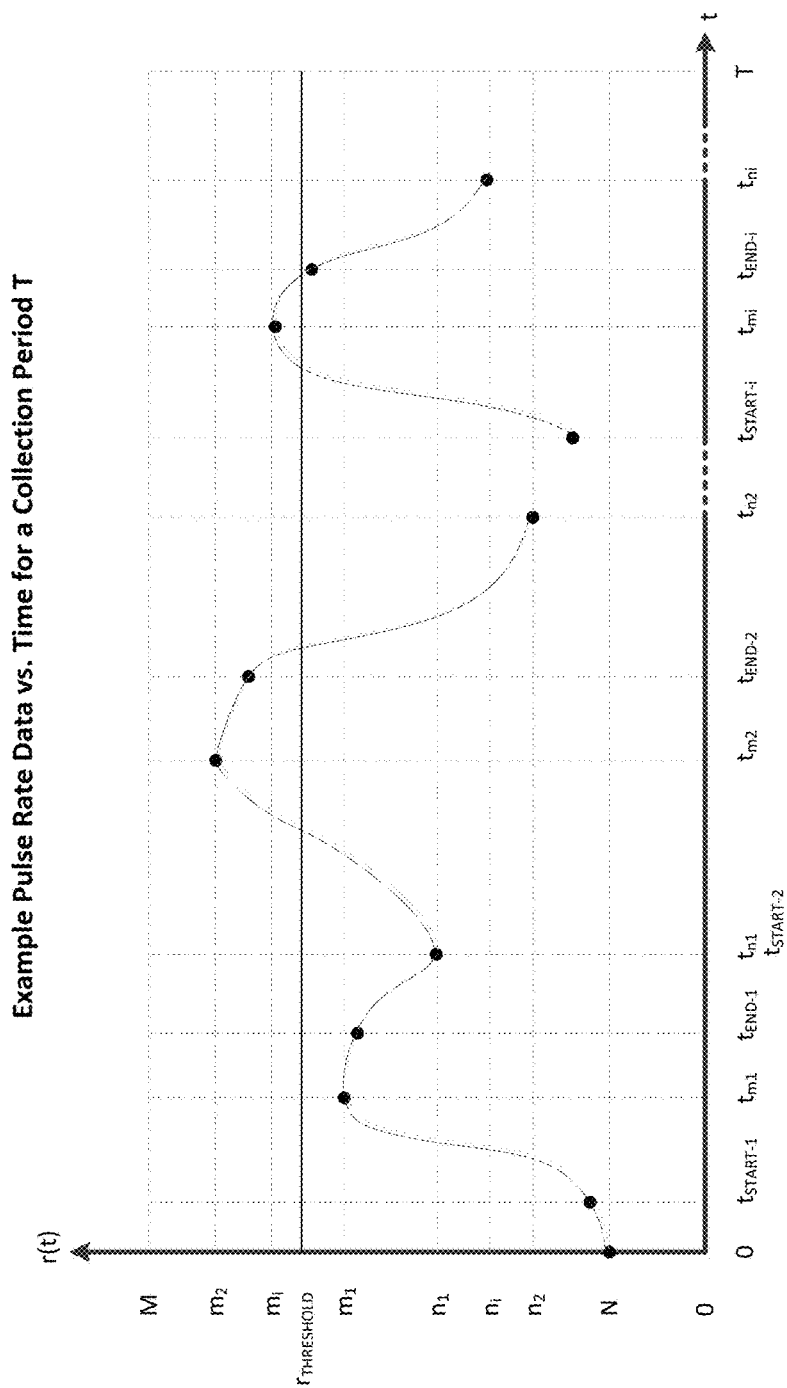
FIG. 4B illustrates a graph of pulse rate for the example data collection period of FIG. 4A.

FIGS. 4A-B illustrate an example data collection period T. The data collection period T begins at time t=0, when the subject's pulse rate r may be at or near the resting pulse rate N. At time t=$t_{START-1}$, the subject engages in non-prescribed physical activity during a first physical activity period $AP_1$ and correspondingly the pulse rate r begins to increase. For instance, the first physical activity period $AP_1$ may involve exercising by running through the neighborhood. At a time t=$t_{m1}$, the pulse rate r reaches a maximum pulse rate $m_1$ for the first physical activity period $AP_1$. At time t=$t_{END-1}$, the first physical activity period $AP_1$ ends and the subject ceases the physical activity. The pulse rate r decreases over a first recovery period $RP_1$ from the time t=$t_{END-1}$ and reaches a minimum pulse rate $n_1$ at time t=$t_{n1}$.

At a later time t=$t_{START-2}$, the subject engages in further physical activity during a second physical activity period $AP_2$ and the pulse rate r begins to increase again. As shown in FIG. 4B, the second physical activity period $AP_2$ interrupts the first recovery period $RP_1$. In alternative cases, however, the second physical activity period $AP_2$ may occur well after the first recovery period $RP_1$.

The second physical activity period $AP_2$ may involve a different type of activity from the first physical activity period $AP_1$. For instance, the second physical activity period $AP_2$ may involve cycling. Alternatively, the second physical activity period $AP_2$ may involve the same type of activity as the first physical activity period $AP_1$. For instance, the physical activity periods $AP_1$ and $AP_2$ may both involve running, and the first recovery period $RP_1$ involves a break during the running. Such a break, for example, may occur as the subject is waiting for traffic to stop in order to cross a street.

At a time t=$t_{m2}$, the pulse rate r reaches a maximum pulse rate $m_2$ for the second physical activity period $AP_2$. At time t=$t_{END-2}$, the subject ends second physical activity period $AP_2$. The pulse rate decreases over a second recovery period $RP_2$ from the time t=$t_{END-2}$ and reaches a minimum pulse rate $n_2$ at time $t_{n2}$.

In general, the subject may generally experience any number of physical activity periods $AP_{i=1, 2, \ldots, n}$ during the data collection period T. Each physical activity period $AP_i$ begins at time t=time$_{START-i}$. At a time t=t$_{mi}$, the pulse rate r reaches a maximum pulse rate m$_i$ for the respective physical activity AP$_i$. At time t=t$_{END-i}$, the subject ends the physical activity period AP$_i$. The pulse rate r decreases over a recovery period RP$_i$ from the time t=t$_{END-i}$ and reaches a minimum pulse rate n$_i$ at time t=t$_{ni}$. In some cases, the recovery period RP$_i$ may be interrupted by a subsequent physical activity period AP$_{(i+1)}$, so that the pulse rate n$_i$ may not decrease completely to the resting pulse rate N. In other cases, the subsequent physical activity period AP$_{(n+1)}$ may occur well after the recovery period RP$_i$, so that the pulse rate n$_i$ may decrease substantially to the resting pulse rate N.

As shown in FIG. 4B, the pulse rate as a function of time, r(t), may increase according to different slopes during any of the physical activity periods AP$_i$. For instance, while running during the first physical activity period AP$_1$, the subject's pace may speed up or slow down causing the slope to increase or decrease correspondingly. Similarly, the pulse rate as a function of time, r(t), may decrease according to different slopes during any of the recovery periods RP$_i$. For instance, if the subject is recovering from running during the first recovery period RP$_1$, the subject may stand or sit still or walk intermittently. When the subject is standing or sitting still, the subject's pulse rate r may decrease more quickly than when the subject walks.

As shown in FIG. 4B, unlike the clinical procedure described above, the maximum pulse rates m$_i$ might not be equal to the subject's peak pulse rate M. In general, the maximum pulse rates m$_i$ are local maxima corresponding to the respective physical activity period AP$_i$. Moreover, the subject might not maintain the maximum pulse rate m$_i$ for an extended period of time.

As shown additionally in FIG. 4B, the pulse rate r$_{ni}$ might not equal the resting pulse rate N if the subject starts another physical activity that increases the pulse rate r before the pulse rate r reaches the resting pulse rate N. In general, the minimum pulse rates n$_i$ are local minima corresponding to the respective recovery periods RP$_i$.

As described above, the first physical activity period AP$_1$ may involve running and the second physical activity period AP$_2$ may involve cycling. The physical activity during each period AP$_i$, however, is not limited to one type of physical activity. For instance, a third physical activity period AP$_3$ may involve a combination of physical activities, e.g., both running and cycling, which causes the pulse rate r to increase to a maximum pulse rate m$_3$. In general, the subject may experience any number of physical activity periods AP$_{i=1, 2, \ldots, n}$ and each physical activity period AP$_i$ may include any combination of physical activities.

The example monitoring system 100 includes monitoring devices 110 that may be conveniently and easily worn by the subject during physical activities outside a clinical setting. In particular, the monitoring devices 110 may include the ECG sensor 110a and/or the PPG sensor 110b to collect pulse rate data. Accordingly, the monitoring devices 110 can collect the pulse rate data continuously over the data collection period T. Alternatively, the monitoring devices 110 can be selectively activated to collect the pulse rate data when the subject is actually experiencing physical exertion during the data collection period T. The monitoring devices 110 can be manually activated by the subject prior to a physical activity period AP$_i$. Alternatively, the monitoring devices 110 can be automatically activated by the controller 120, for instance, when it detects certain movement by the subject with another sensor.

As described above, the controller 120 and/or the external system 140 receive the pulse rate data collected by the monitoring devices 110. In particular, the ECG sensor 110a provides the ECG data 10a and the PPG sensor 110b provides the PPG data 10b, as shown in FIG. 1. The controller 120 and/or the external system 140 may execute program instructions stored on computer-readable media to process the data 10a and/or b and determine information regarding the subject's pulse rate recovery. For instance, the at least one data storage device 122 may store program instructions that can be executed by the at least one processor 121 of the controller 120 to manage and process the collection of pulse rate data by the cardiovascular monitoring devices 110. If the monitoring devices 110 include more that one set of data, e.g., the ECG data 10a and the PPG data 10b, the data may be combined or otherwise processed and reconciled to provide one set of pulse rate data for further analysis.

Figure 5A:
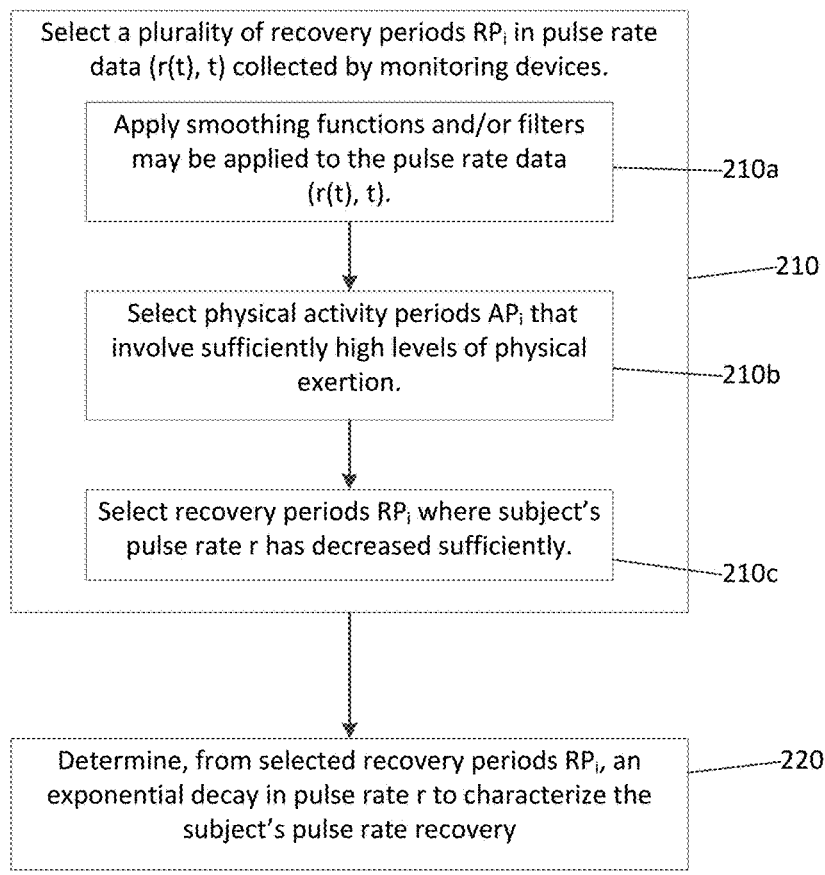
FIG. 5A illustrates an example process for determining pulse rate recovery.

FIG. 5A illustrates an example process 200, which can be employed by the controller 120 and/or the external system 140 to process the pulse rate data and determine the subject's pulse rate recovery. The process 200 may include a first phase 210 that selects recovery periods RP$_i$ in the collected pulse rate data, and a second phase 220 that determines an exponential decay in pulse rate r during the selected recovery periods RP$_i$ to characterize the subject's pulse rate recovery.

As described above, the ability for the subject to recover from physical exertion can be characterized by an exponential decay in pulse rate. In this case, however, the process 200 can determine this exponential decay even though the subject might not experience peak pulse rate M during physical activity or might not recover to the resting pulse rate N after physical activity.

Figure 6A:
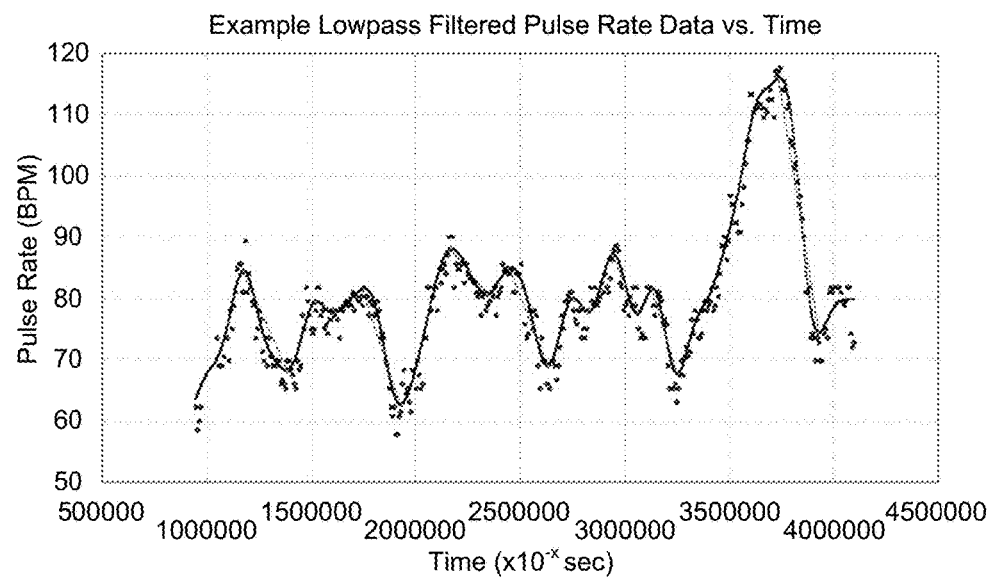
FIG. 6A illustrates an example set of pulse rate data where a lowpass filter has been applied.

The pulse rate data from each monitoring device 110 may include a plurality of data points expressing a measured pulse rate r at a given time t, i.e., (r(t), t). The pulse rate data may be resampled to account for variations in sampling rate. In addition, smoothing functions and/or filters may be applied to the pulse rate data in step 210a to reduce the effect of noise and other fine-scale phenomena that may obscure more significant patterns in the pulse rate data. For instance, the step 210a may resample the pulse rate data and apply a tenth order Butterworth filter with a cutoff frequency of (0.025*Nyquist frequency), where the Nyquist frequency is determined from the resampling d$_{grid}$ spacing and constrained by the rate of output of the Viterbi estimator. FIG. 6A illustrates an example set of pulse rate data, where the lowpass filtered pulse rate data are shown on the curve and the Viterbi pulse rate predictions are shown as plotted points.

Once the pulse rate data has been processed in step 210a, the process 200 applies criteria to identify recovery periods RP$_i$ that provide sufficient information to characterize the subject's pulse rate recovery. As described above, the recovery periods RP$_i$ correspond to decreases in pulse rate r. As such, the recovery periods RP$_i$ can be identified as the time periods where the derivative of the lowpass filtered pulse rate data is consistently negative:

$$\frac{dr(t)}{dr} < 0, \tag{2}$$

or close to negative:

$$\frac{dr(t)}{dt} < \varepsilon, \text{ where } 0 < \varepsilon \ll 1. \tag{3}$$

Figure 6B:
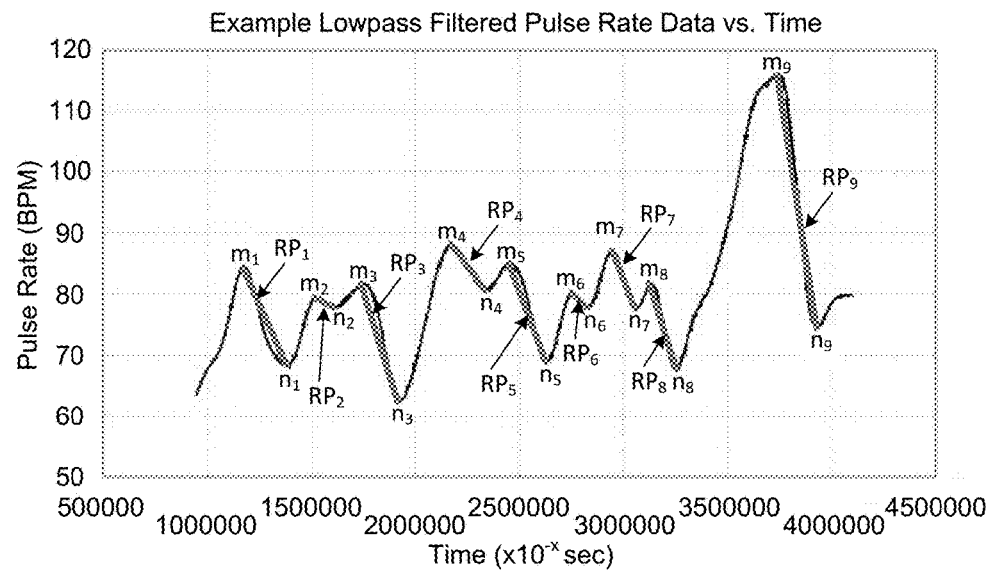
FIG. 6B illustrates the recovery time periods in the pulse rate data of FIG. 6A.

FIG. 6B highlights the recovery time periods in the data of FIG. 6A, where the filtered pulse rate data is consistently negative or close to negative. The time periods generally start at the maximum pulse rate $m_i$ and end at the minimum pulse rate $n_i$.

In the clinical procedure described above, the analysis of pulse rate recovery involves evaluation of the subject's recovery after reaching the peak pulse rate M, i.e., the highest possible pulse rate r for the subject. In a non-clinical setting without instructions from a medical practitioner, the subject might not engage in the maximum level of physical exertion required to achieve the peak pulse rate M. As such, step 210b selects physical activity periods $AP_i$ that involve sufficiently high levels of physical exertion, even if the subject does not fully achieve the peak pulse rate M.

Furthermore, in the clinical procedure described above, the analysis of pulse rate recovery involves evaluation of the subject's pulse rate r as it decreases from the peak pulse rate M to the resting pulse rate N. For instance, the resting pulse rate N at a given time may occur at or near the subject's lowest possible heart rate when the subject is at complete rest after several minutes (e.g., 20 to 30 minutes) of inactivity. In a non-clinical setting without instructions from a medical practitioner, however, the subject might not rest for a sufficient time to achieve the resting pulse rate N after the physical exertion. As such, step 210c selects recovery periods $RP_i$ where the subject's pulse rate r has decreased sufficiently even if the pulse rate r does not reach the resting pulse rate N.

Figure 5B:
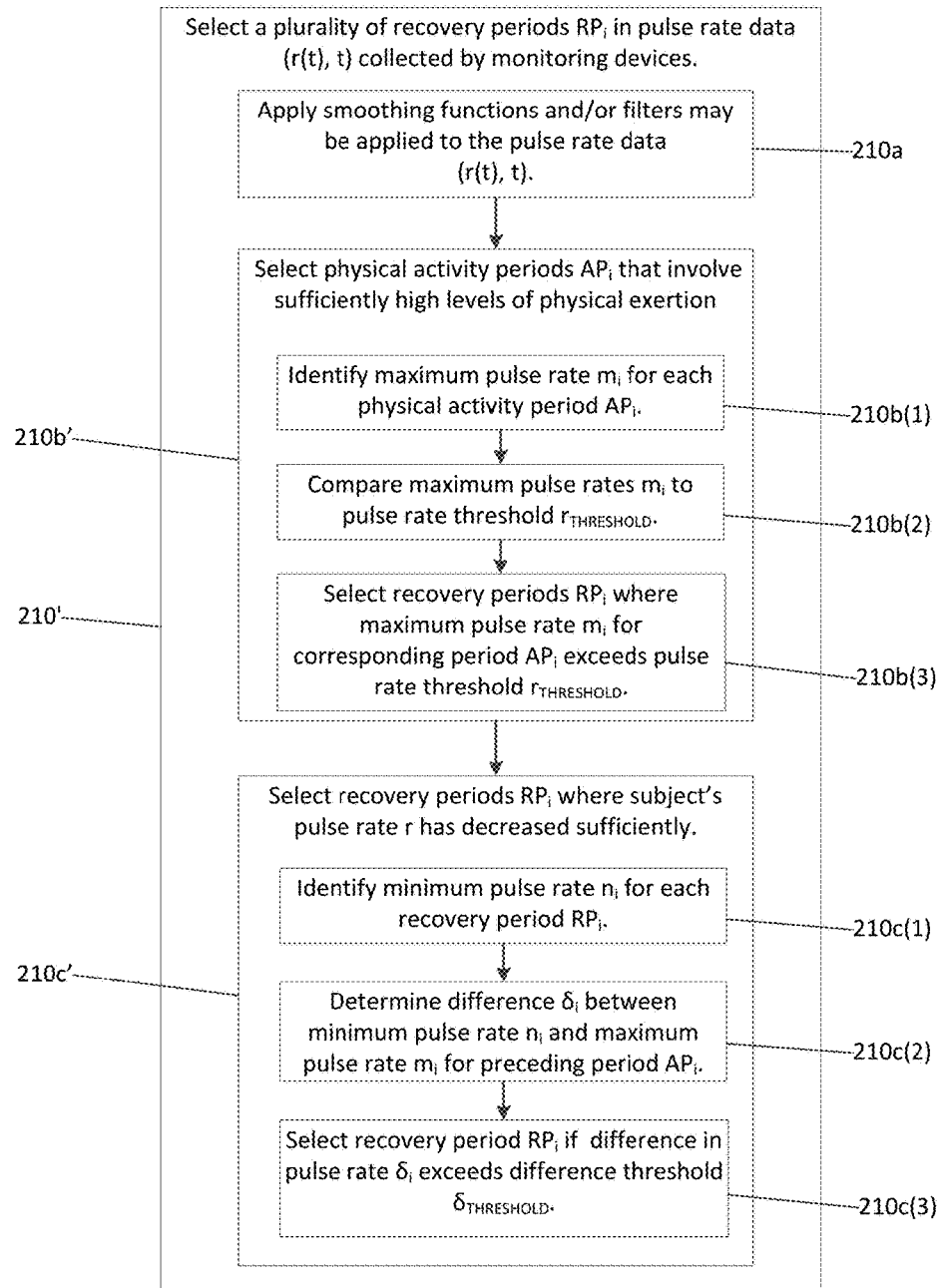
FIG. 5B illustrates a further example process for determining pulse rate recovery.

FIG. 5B illustrates an example embodiment 210' for the step 210 in the process 200. In particular, for step 210(b), step 210b(1) identifies the maximum pulse rate $m_i$ for each physical activity period $AP_i$ and step 210b(2) compares the maximum pulse rates $m_i$ to a pulse rate threshold $r_{THRESHOLD}$. When the maximum pulse rate $m_i$ for a physical activity period $AP_i$ exceeds the pulse rate threshold $r_{THRESHOLD}$, the subject experiences a sufficiently high level of exertion for effective evaluation of pulse rate recovery. As a result, step 210b(3) selects recovery periods $RP_i$ where the maximum pulse rate $m_i$ for the corresponding physical activity period $AP_i$ exceeds the pulse rate threshold $r_{THRESHOLD}$.

The pulse rate threshold $r_{THRESHOLD}$ may be set to some percentage, e.g., 80%, 90%, etc., of the subject's peak pulse rate M and programmed into the process 200. In some cases, a medical practitioner may determine the subject's peak pulse rate M through a clinical procedure. For instance, the peak pulse rate at a given time may occur at or near the subject's highest possible pulse rate in response to the highest possible level of exertion. In other cases, the subject's peak pulse rate M may be determined according to a more general formula. For instance, one such formula involves subtracting the subject's age from 220 to determine the subject's peak pulse rate M.

After selecting the particular recovery periods in steps 210b(1)-(3), step 210c(1) identifies the minimum pulse rate $n_i$ for each recovery period $RP_i$ and step 210c(2) determines a difference $\delta_i$ between the minimum pulse rate $n_i$ and the maximum pulse rate $m_i$ for the preceding physical activity period $AP_i$. If the difference in pulse rate $\delta_i$ exceeds a difference threshold $\delta_{THRESHOLD}$, step 210c(3) selects the respective recovery period $RP_i$ because the subject's pulse rate r has decreased sufficiently to determine the subject's pulse rate recovery more accurately.

For instance, in the example of FIGS. 4A-B, steps 210b (1), (2) may determine that the maximum pulse rate $m_1$ for the first physical activity $AP_1$ fails to exceed the pulse rate threshold $r_{THRESHOLD}$. This indicates that the subject has not experienced a sufficiently high level of physical exertion during the first physical activity $AP_1$. Because the maximum pulse rate $m_1$ fails to meet the threshold $r_{THRESHOLD}$, step 210b(3) may eliminate the corresponding recovery period $RP_1$ from further analysis On the other hand, steps 210b(1), (2) may determine that the maximum pulse rate $m_2$ for the second physical activity $AP_2$ exceeds the pulse rate threshold $r_{THRESHOLD}$. This indicates that the subject has experienced a sufficiently high level of physical exertion during the second physical activity $AP_2$. Step 210c(1) may then identify the minimum pulse rate $n_2$ for the recovery period $RP_2$ and step 210c(2) may subtract $m_2$ from $n_2$ to determine the difference $\delta_2$. If the difference $\delta_2$ exceeds the difference threshold $\delta_{THRESHOLD}$, step 210c (3) selects the recovery period $RP_2$ because the subject's heart rate r has decreased sufficiently for more effective evaluation of the subject's pulse rate recovery.

Accordingly, the first phase 210 processes the pulse rate data and identifies recovery periods $RP_i$ that correspond to sufficient levels of physical exertion and provide sufficient information to evaluate the subject's pulse rate recovery effectively. Each recovery period $RP_i$ may be characterized by the corresponding maximum pulse rate $m_i$, the minimum pulse rate $n_i$, as well as the difference $\delta_i$ between $n_i$ and $m_i$, i.e., $(m_i, n_i, \delta_i)$.

For the recovery periods $RP_i$ selected in the first phase 210, the second phase 220 then determines an exponential decay in pulse rate r. In particular, equation (1) above is modified to:

$$r(t)=N'+(M'-N')e^{-(t/\tau)} \quad (4)$$

where:

$$M'=\max(m_i) \quad (5),$$

$$N'=\min(n_i) \quad (6).$$

Accordingly, with $$\mu=\log((m_i-N')/(M'-N')) \quad (7),$$

$$l=\log((n_i-N')/(M'-N')) \quad (8),$$

the exponential time constant $\tau$ (inverse of decay constant $\lambda$) can be found with the data $(m_i, n_i, \delta_i)$ for the recovery periods $RP_i$ by determining the solution, e.g., the least-squares solution, to:

$$(\mu-l)*\tau=-\delta_i \quad (9).$$

Generally, the selected recovery periods $RP_i$ each show substantially similar exponential decay. As such, the recovery periods periods $RP_i$ can be employed to solve equation (9), and the resulting exponential time constant $\tau$ generally reflects the exponential decay in the subject's pulse rate r after any physical activity. A faster pulse rate recovery, i.e., exponential decay, indicates that the subject can recover more quickly from physical exertion due to better cardiovascular health. In other words, the exponential time constant $\tau$ provides a measure of the subject's cardiovascular health during the data collection period T.

The exponential time constant $\tau$ as well as other aspects of the process 200 may be displayed or otherwise presented via the controller 120 (e.g., the user interface 125) and/or the external system 140. The medical practitioner can access this data to evaluate the subject's cardiovascular health. Additionally or alternatively, the subject may track his/her own pulse rate recovery.

The subject's pulse rate recovery as measured by the exponential time constant $\tau$ may be tracked over time to identify any changes in the subject's cardiovascular health.

Figure 7:
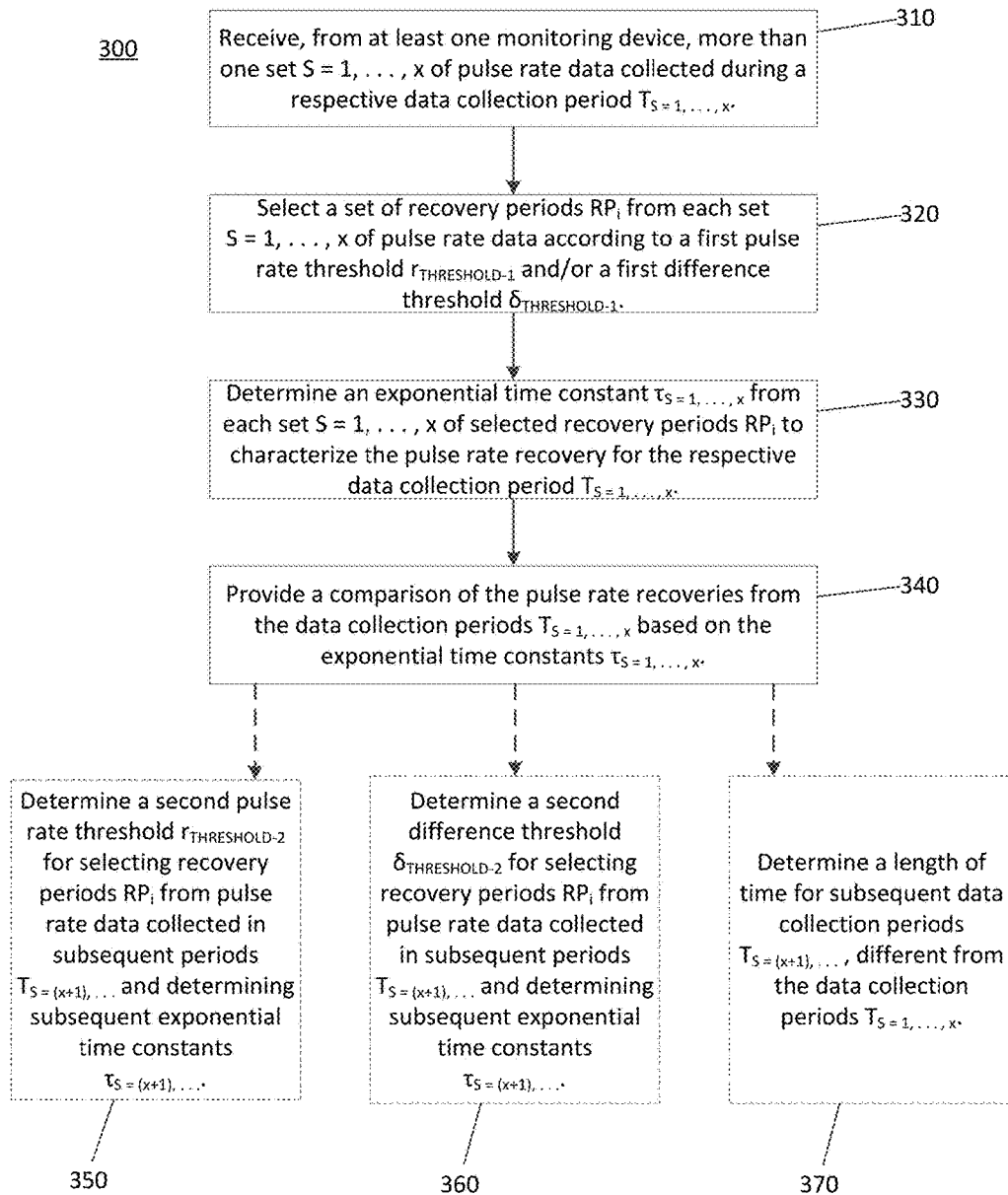
FIG. 7 illustrates another example process for determining pulse rate recovery.

For instance, in an example process 300 shown in FIG. 7, step 310 may receive, from at least one monitoring device, more than one set $S=1, \ldots, x$ of pulse rate data from a subject. Each set $S=1, \ldots, x$ of pulse rate data is collected during a respective data collection period $T_{S=1, \ldots, x}$. Step 320 selects a set of recovery periods $RP_i$ from each set $S=1, \ldots, x$ of pulse rate data. Each recovery period $RP_i$ corresponds to a respective decrease in pulse rate from a respective maximum pulse rate $m_i$ to a respective minimum pulse rate $n_i$. The respective maximum pulse rate $m_i$ is less than the peak pulse rate M of the subject or the respective minimum pulse rate $n_i$ is greater than the resting pulse rate N of the subject. Step 330 determines an exponential time constant $\tau_{S=1, \ldots, x}$ from each set $S=1, \ldots, x$ of selected recovery periods $RP_i$ to characterize the pulse rate recovery for the respective data collection period $T_{S=1, \ldots, x}$. Step 340 provides a comparison of the pulse rate recoveries from the data collection periods $T_{S=1, \ldots, x}$ based on the exponential time constants $\tau_{S=1, \ldots, x}$.

The exponential time constants $\tau$ determined from a plurality of data collection periods T may also be evaluated to validate and/or improve the process 200. For instance, if the different exponential time constants $\tau$ remain relatively consistent or indicate reasonable changes in cardiovascular health, the process 200 is probably providing data that accurately reflects the subject's pulse rate recovery. On the other hand, if the different exponential time constants T appear to vary inconsistently or do not indicate reasonable changes in cardiovascular health, the process 200 might be improved by modifying the pulse rate threshold $r_{THRESHOLD}$, modifying the difference threshold $\delta_{THRESHOLD}$, and/or collecting data from more recovery periods $RP_i$. To evaluate the subject's cardiovascular health more accurately, some of the calculated exponential time constants $\tau$ may also be thrown out as statistical outliers due to system errors, etc.

In some cases, data from certain recovery periods $RP_i$ may be weighted more greatly if the recovery periods $RP_i$ are more likely to reveal the exponential decay of the subject's pulse rate. For instance, the process 200 may place greater weight on data from recovery periods $RP_i$ that occur after physical activity periods $AP_i$ with greater maximum pulse rates $m_i$ and/or that have greater pulse rate differences $\delta_i$. Indeed, pulse rate thresholds and/or the difference thresholds similar to those described above may be employed to determine weightings for the data from recovery periods $RP_i$. Additionally or alternatively, the process 200 may place greater weight on data from recovery periods $RP_i$ that occur after certain types of classified activity, such as running as opposed to walking.

In some cases, the pulse rate threshold $r_{THRESHOLD}$ and the difference threshold $\delta_{THRESHOLD}$ may be modified due to changes in the subject's cardiovascular health over time. In the example process 300 of FIG. 7, the exponential time constants $\tau_{S=1, \ldots, x}$ may be determined from respective recovery periods $RP_i$ that are selected in step 320 according to a first pulse rate threshold $r_{THRESHOLD\text{-}1}$ and/or a first difference threshold $\delta_{THRESHOLD\text{-}1}$ as described above. Based on the comparison of the exponential time constants $\tau_{S=1, \ldots, x}$ in step 340, step 350 may determine a second pulse rate threshold $r_{THRESHOLD\text{-}2}$ for selecting recovery periods $RP_i$ from pulse rate data collected in subsequent periods $T_{S=(x+1) \ldots}$ and determining subsequent exponential time constants $\tau_{S=(x+1), \ldots}$. For instance, the comparison of the exponential time constants $\tau_{S=1, \ldots, x}$ may show that the subject's cardiovascular health improved between the data collection period $T_1$ and the data collection period $T_x$. As such, the pulse rate threshold may be increased from $r_{THRESHOLD\text{-}1}$ to $r_{THRESHOLD\text{-}2}$ for evaluation of subsequent exponential time constants $\tau_{S=(x+1) \ldots}$.

Additionally or alternatively, based on the comparison of the exponential time constants $\tau_{S=1, \ldots, x}$ in step 340, step 360 may determine a second difference threshold $\delta_{THRESHOLD\text{-}2}$ for selecting recovery periods $RP_i$ from pulse rate data collected in subsequent periods $T_{S=(x+1), \ldots}$ and determining subsequent exponential time constants $\tau_{S=(x+1), \ldots}$. The comparison may show that the assessment of pulse rate recovery may be improved by employing a second difference threshold $\delta_{THRESHOLD\text{-}2}$. For instance, the second difference threshold $\delta_{THRESHOLD\text{-}2}$ may provide pulse rate data from longer recovery periods that provide greater indication of exponential decay.

Additionally or alternatively, based on the comparison of the exponential time constants $T_{S=1, \ldots, x}$ in step 340, step 370 may determine that subsequent data collection periods $T_{S=(x+1), \ldots}$ should extend over a length of time that is different from the data collection periods $T_{S=1, \ldots, x}$. For instance, the length of the data collection periods T may be selected to determine the effect of other changes in the the subject's lifestyle, such as weekly changes in the subject's diet, medication, and/or exercise routine. As such, it may be determined that length of time for subsequent collection periods $T_{S=(x+1), \ldots}$ may be shortened or lengthened from prior data collection periods $T_{S=1, \ldots, x}$ to capture the effect of such changes more effectively.

IV. CONCLUSION

In view of the foregoing, example systems can robustly and accurately collect data relating to a subject's cardiovascular function. The example systems can collect pulse rate data when the subject is engaged in non-prescribed physical activities in a non-clinical environment. The example systems can identify recovery periods after the subject experiences physical exertion during such activities. By evaluating the decrease in pulse rate during these recovery periods (known as pulse rate recovery), the example systems can determine the subject's ability to recover from the physical exertion and assess the subject's cardiovascular health. The example systems can assess the pulse rate recovery even if the pulse rate does reach the subject's peak pulse rate during the physical activities and/or the pulse rate does not decrease to the resting pulse rate during the recovery periods. In particular, the example systems can select a plurality of recovery periods according to certain criteria and fit the data from these recovery periods into a model to determine an exponential decay that accurately characterizes the pulse rate recovery.

The embodiments described herein employ devices for processing information and controlling aspects of the example systems, e.g., the controller 120. Such devices may be implemented as a combination of hardware and software elements. The hardware elements may include combinations of operatively coupled hardware components, including microprocessors, memory, signal filters, circuitry, etc. The processors may be configured to perform operations specified by the software elements, e.g., computer-executable code stored on computer readable medium. The processors may be implemented in any device, system, or subsystem to provide functionality and operation according to the present disclosure. The processors may be implemented in any number of physical devices/machines. Indeed, parts of the processing of the example embodiments can be distributed over any combination of processors for better performance, reliability, cost, etc.

The physical devices/machines can be implemented by the preparation of integrated circuits or by interconnecting an appropriate network of conventional component circuits, as is appreciated by those skilled in the electrical art(s). The physical devices/machines, for example, may include field programmable gate arrays (FPGA's), application-specific integrated circuits (ASIC's), digital signal processors (DSP's), etc.

Appropriate software can be readily prepared by programmers of ordinary skill based on the teachings of the example embodiments, as is appreciated by those skilled in the software arts. Thus, the example embodiments are not limited to any specific combination of hardware circuitry and/or software. Stored on one computer readable medium or a combination of computer readable media, the computing systems may include software for controlling the devices and subsystems of the example embodiments, for driving the devices and subsystems of the example embodiments, for enabling the devices and subsystems of the example embodiments to interact with a human user (user interfaces, displays, controls), etc. Such software can include, but is not limited to, device drivers, operating systems, development tools, applications software, etc. A computer readable medium further can include the computer program product(s) for performing all or a portion of the processing performed by the example embodiments. Computer program products employed by the example embodiments can include any suitable interpretable or executable code mechanism, including but not limited to complete executable programs, interpretable programs, scripts, dynamic link libraries (DLLs), applets, etc. The processors may include, or be otherwise combined with, computer-readable media. Some forms of computer-readable media may include, for example, a hard disk, any other suitable magnetic medium, any suitable optical medium, RAM, PROM, EPROM, flash memory, any other suitable memory chip or cartridge, any other suitable non-volatile memory, a carrier wave, or any other suitable medium from which a computer can read.

The processing/control devices may also include databases for storing data. Such databases may be stored on the computer readable media described above and may organize the data according to any appropriate approach. For examples, the data may be stored in relational databases, navigational databases, flat files, lookup tables, etc.

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A system for assessing cardiovascular health, comprising:
   one or more monitoring devices configured to collect pulse rate data from a subject, the pulse rate data including pulse rate measurements and corresponding measurement timestamps, each of the one or more monitoring devices including a first communication interface; and
   a controller including:
      one or more second communication interfaces, each second communication interface configured to be communicatively coupled to at least one of the one or more monitoring devices via the corresponding first communication interfaces and to receive the corresponding pulse rate data from the at least one of the one or more monitoring devices;
      at least one data storage device configured to store the pulse rate data on the at least one data storage device; and
      at least one processor configured to:
         (a) select a plurality of recovery periods in the pulse rate data, each recovery period corresponding to a respective decrease in pulse rate from a respective upper pulse rate to a respective lower pulse rate, wherein the respective upper pulse rate is less than a peak pulse rate of the subject or the respective lower pulse rate is greater than a resting pulse rate of the subject;
         (b) determine an exponential decay from the plurality of selected recovery periods, the exponential decay characterizing a pulse rate recovery for the subject; and
         (c) provide, via a user interface, the pulse rate recovery for the subject based on the exponential decay.

2. The system of claim 1, wherein the at least one processor is further configured to determine if the respective upper pulse rate of a given recovery period is greater than a pulse rate threshold, the pulse rate threshold indicating a minimum level of physical exertion by the subject, and
   in response to the respective upper pulse rate of the given recovery period being greater than the pulse rate threshold, the at least one processor selects the given recovery period to determine the exponential decay.

3. The system of claim 1, wherein the at least one processor is further configured to determine if the respective decrease in pulse rate for a given recovery period is greater than a difference threshold, the difference threshold indicating a minimum level of recovery by the subject after physical exertion, and
   in response to the respective decrease in pulse rate of the given recovery period being greater than the difference threshold, the at least one processor selects the given recovery period to determine the exponential decay.

4. The system of claim 1, wherein the at least one processor is further configured to at least one of resample the pulse rate data to account for variations in sampling rate, or apply a smoothing function or a filter to the pulse rate data.

5. The system of claim 1, wherein each selected recovery period $RP_i$ is characterized by the respective upper pulse rate the respective lower pulse and the respective decrease in pulse rate $\delta_i$, and the at least one processor determines the exponential decay by solving for the exponential time constant $\tau$ in $(\mu-1)*\tau=-\delta_i$ with $(m_i, n_i, \delta_i)$ for each selected recovery period $RP_i$, where $\mu=\log((m_i-N')/(M'-N'))$, and $l=\log((n_i-N')/(M'-N'))$, M' being a maximum of the upper pulse rates $m_i$, and N' being a minimum of the lower pulse rates $n_i$.

6. The system of claim 1, wherein the one or more monitoring devices includes an electrocardiography (ECG) sensor or a photoplethysmography (PPG) sensor.

7. A method for assessing cardiovascular health, comprising:

receiving, from one or more monitoring devices, pulse rate data from a subject, the pulse rate data including pulse rate measurements and corresponding measurement timestamps;

storing the pulse rate data on at least one data storage device;

selecting, with at least one processor, a plurality of recovery periods in the pulse rate data, each recovery period corresponding to a respective decrease in pulse rate from a respective upper pulse rate to a respective lower pulse rate, wherein the respective upper pulse rate is less than a peak pulse rate of the subject or the respective lower pulse rate is greater than a resting pulse rate of the subject;

determining, with the at least one processor, an exponential decay from the plurality of selected recovery periods, the exponential decay characterizing a pulse rate recovery for the subject; and providing, via a user interface, the pulse rate recovery for the subject based on the exponential decay.

8. The method of claim 7, further comprising determining, with the at least one processor, if the respective upper pulse rate of a given recovery period is greater than a pulse rate threshold, the pulse rate threshold indicating a minimum level of physical exertion by the subject, wherein the at least one processor selects the given recovery period to determine the exponential decay in response to the respective upper pulse rate of the given recovery period being greater than the pulse rate threshold.

9. The method of claim 7, further comprising determining, with the at least one processor, if the respective decrease in pulse rate for a given recovery period is greater than a difference threshold, the difference threshold indicating a minimum level of recovery by the subject after physical exertion, wherein the at least one processor selects the given recovery period to determine the exponential decay in response to the respective decrease in pulse rate of the given recovery period being greater than the difference threshold.

10. The method of claim 7, wherein determining the exponential decay from the plurality of selected recovery periods includes weighting each selected recovery period according to at least one of the respective upper pulse rate, the respective lower pulse rate, and the respective decrease in pulse rate.

11. The method of claim 7, further comprising at least one of:

resampling, with the at least one processor, the pulse rate data to account for variations in sampling rate, or applying a smoothing function or a filter to the pulse rate data.

12. The method of claim 7, wherein each selected recovery period $RP_i$ is characterized by the respective upper pulse rate $m_i$, the respective lower pulse rate $n_i$, and the respective decrease in pulse rate $\delta_i$, and the at least one processor determines the exponential decay by solving for the exponential time constant $\tau$ in $(\mu-1)*\tau=-\delta_i$ with $(m_i, n_i, \delta_i)$ for each selected recovery period $RP_i$, where $\mu=\log((m_i-N')/(M'-N'))$, and $l=\log((n_i-N')/(M'-N'))$, M' being a maximum of the upper pulse rates $m_i$, and N' being a minimum of the lower pulse rates $n_i$.

13. A method for assessing cardiovascular health, comprising:

receiving, from at least one monitoring device, more than one set of pulse rate data from a subject, each set of pulse rate data collected during a respective data collection period and including pulse rate measurements and corresponding measurement timestamps;

selecting, with at least one processor, a set of recovery periods from each set of pulse rate data, each recovery period corresponding to a respective decrease in pulse rate from a respective upper pulse rate to a respective lower pulse rate, wherein the respective upper pulse rate is less than a peak pulse rate of the subject or the respective lower pulse rate is greater than a resting pulse rate of the subject;

determining, with the at least one processor, an exponential decay from each set of selected recovery periods, each exponential decay characterizing a pulse rate recovery for the subject for the respective data collection period; and providing, via a user interface, a comparison of the pulse rate recoveries from the data collection periods based on the exponential decays.

14. The method of claim 13, further comprising determining, with the at least one processor, if the respective upper pulse rate of a given recovery period is greater than a first pulse rate threshold, the first pulse rate threshold indicating a first minimum level of physical exertion by the subject, wherein the at least one processor selects the given recovery period to determine the exponential decay for the respective data collection period, in response to the respective upper pulse rate of the given recovery period being greater than the pulse rate threshold.

15. The method of claim 14, further comprising:

in response to the comparison of the pulse rate recoveries, determining, with the at least one processor, a second pulse rate threshold, the second pulse rate threshold indicating a second minimum level of physical exertion by the subject;

receiving, from the at least one monitoring device, an additional set of pulse rate data from the subject collected during an additional data collection period, the additional set of pulse rate data including additional pulse rate measurements and corresponding measurement timestamps;

selecting, with the at least one processor, an additional set of recovery periods from the additional set of pulse rate data, wherein the at least one processor:

(a) determines if the respective upper pulse rate of a given recovery period in the additional set of pulse rate data is greater than a second pulse rate threshold, and (b) selects the given recovery period from the additional set of pulse rate data in response to the respective upper pulse rate being greater than the second pulse rate threshold;

determining, with the at least one processor, an additional exponential decay from the additional set of selected recovery periods; and providing, via a user interface, an additional pulse rate recovery for the subject based on the additional exponential decay.

16. The method of claim 13, further comprising determining, with the at least one processor, if the respective decrease in pulse rate of a given recovery period is greater than a first difference threshold, the first difference threshold indicating a first minimum level of recovery by the subject after physical exertion, wherein the at least one processor selects the given recovery period to determine the exponential decay for the respective data collection period, in response to the respective decrease in pulse rate of the given recovery period being greater than the first difference threshold.

17. The method of claim 16, further comprising:

in response to the comparison of the pulse rate recoveries, determining, with the at least one processor, an additional data collection period;

receiving, from the at least one monitoring device, an additional set of pulse rate data from the subject collected during the additional data collection period, the additional set of pulse rate data including additional pulse rate measurements and corresponding measurement timestamps;

selecting, with the at least one processor, an additional set of recovery periods from the additional set of pulse rate data, wherein the at least one processor:

(a) determines if the respective decrease in pulse rate of a given recovery period in the additional set of pulse rate data is greater than a second difference threshold, and (b) selects the given recovery period from the additional set of pulse rate data in response to the respective decrease in pulse rate being greater than the second difference threshold;

determining, with the at least one processor, an additional exponential decay from the additional set of selected recovery periods; and providing, via a user interface, an additional pulse rate recovery for the subject based on the additional exponential decay.

18. The method of claim 13, wherein the respective data collection periods extend over a substantially similar first length of time.

19. The method of claim 18, further comprising:

in response to the comparison of the pulse rate recoveries, determining, with the at least one processor, an additional data collection period extending over a second length of time that is different from the first length of time;

receiving, from the at least one monitoring device, an additional set of pulse rate data from the subject collected during the additional data collection period, the additional set of pulse rate data including additional pulse rate measurements and corresponding measurement timestamps;

selecting, with the at least one processor, an additional set of recovery periods from the additional set of pulse rate data;

determining, with the at least one processor, an additional exponential decay from the additional set of selected recovery periods; and providing, via a user interface, an additional pulse rate recovery for the subject based on the additional exponential decay.

20. The method of claim 13, wherein each selected recovery period $RP_i$ is characterized by the respective upper pulse rate $m_i$, the respective lower pulse $n_i$, and the respective decrease in pulse rate $\delta_i$, and the at least one processor determines the exponential decay for each data collection period by solving for the exponential time constant $\tau$ in $(\mu-l)*\tau=-\delta_i$ with $(m_i, n_i, \delta_i)$ for each selected recovery period $RP_i$ in the corresponding data collection period, where $\mu=\log((m_i-N')/(M'-N'))$, and $l=\log((n_i-N')/(M'-N'))$, M' being a maximum of the upper pulse rates $m_i$, and N' being a minimum of the lower pulse rates $n_i$.

* * * * *